(12) United States Patent
Schulze

(10) Patent No.: US 6,562,053 B2
(45) Date of Patent: May 13, 2003

(54) CURVED MANDREL FOR ASSISTING VESSEL EVERSION

(75) Inventor: Dale R. Schulze, Lebanon, OH (US)

(73) Assignee: Ethicon, Inc., Somerville, NJ (US)

(*) Notice: Subject to any disclaimer, the term of this patent is extended or adjusted under 35 U.S.C. 154(b) by 0 days.

(21) Appl. No.: 09/861,968

(22) Filed: May 21, 2001

(65) Prior Publication Data

US 2002/0173801 A1 Nov. 21, 2002

(51) Int. Cl.⁷ .............................................. A61B 17/04
(52) U.S. Cl. ...................................................... 606/149
(58) Field of Search ................................ 606/149, 148, 606/150, 139, 140, 144

(56) References Cited

U.S. PATENT DOCUMENTS

| | | |
|---|---|---|
| 2,086,371 A | 7/1937 | Tear |
| 2,940,452 A | 6/1960 | Smialowski |
| 3,040,748 A | 6/1962 | Klein et al. |
| 3,057,355 A | 10/1962 | Smialowski et al. |
| 3,180,337 A | 4/1965 | Smialowski |
| 3,908,662 A | 9/1975 | Razgulov et al. |
| 4,470,415 A | 9/1984 | Wozniak |
| 4,622,970 A | 11/1986 | Wozniak |
| 6,287,322 B1 * | 9/2001 | Zhu et al. .................. 606/213 |

* cited by examiner

Primary Examiner—Danny Worrell

(57) ABSTRACT

An instrument is provided for everting an end of a vessel, preferably over an end of a tubular workpiece. The instrument has a curved mandrel having a proximal end and a distal end. The distal end of the curved mandrel is insertable to a predetermined depth into the lumen of the vessel contained in the bore of the workpiece. The curved mandrel holds the vessel against the bore surface of the workpiece at three spaced-apart contact regions when it is inserted into the bore of the workpiece and the vessel lumen to the predetermined depth. The curved mandrel is mounted to a handle.

7 Claims, 4 Drawing Sheets

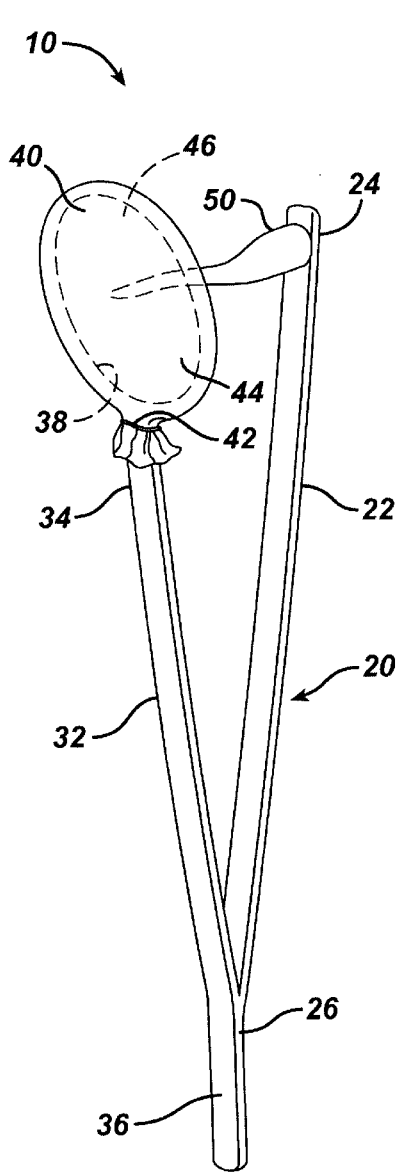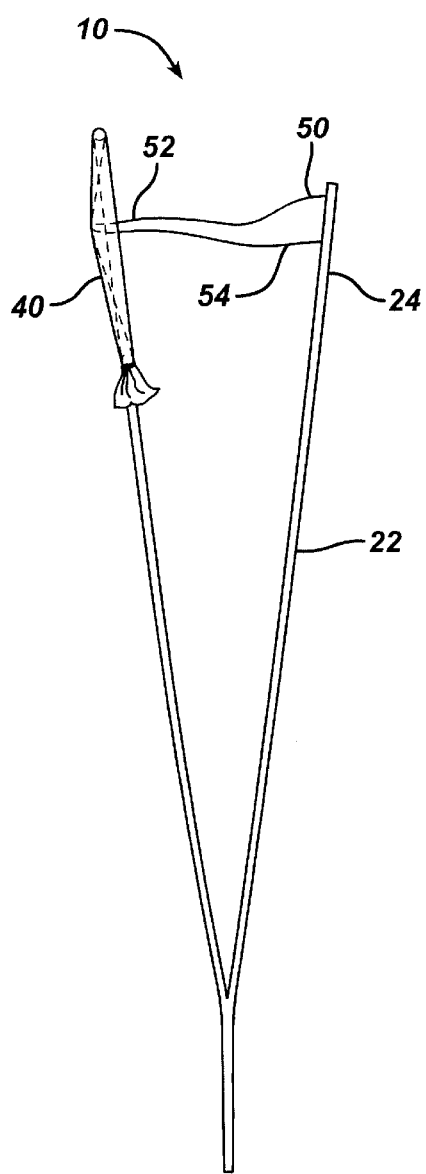
FIG. 1    FIG. 2

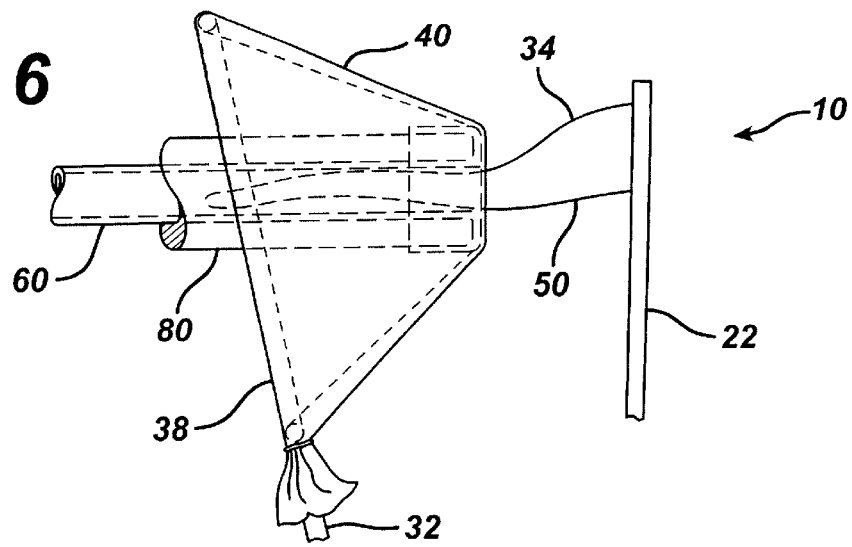
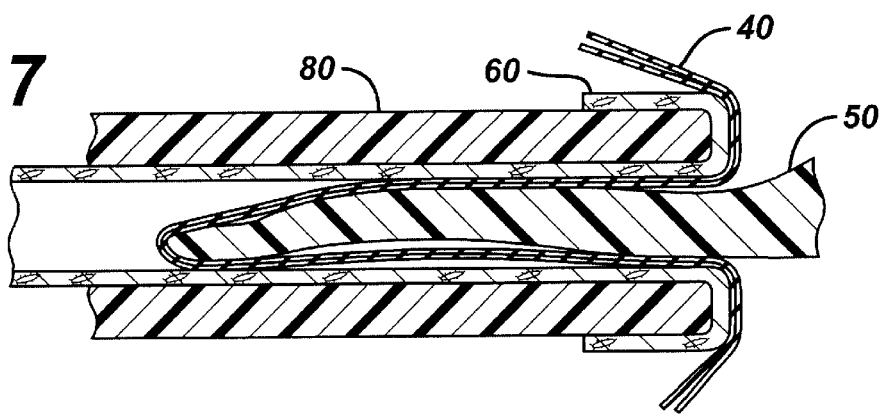
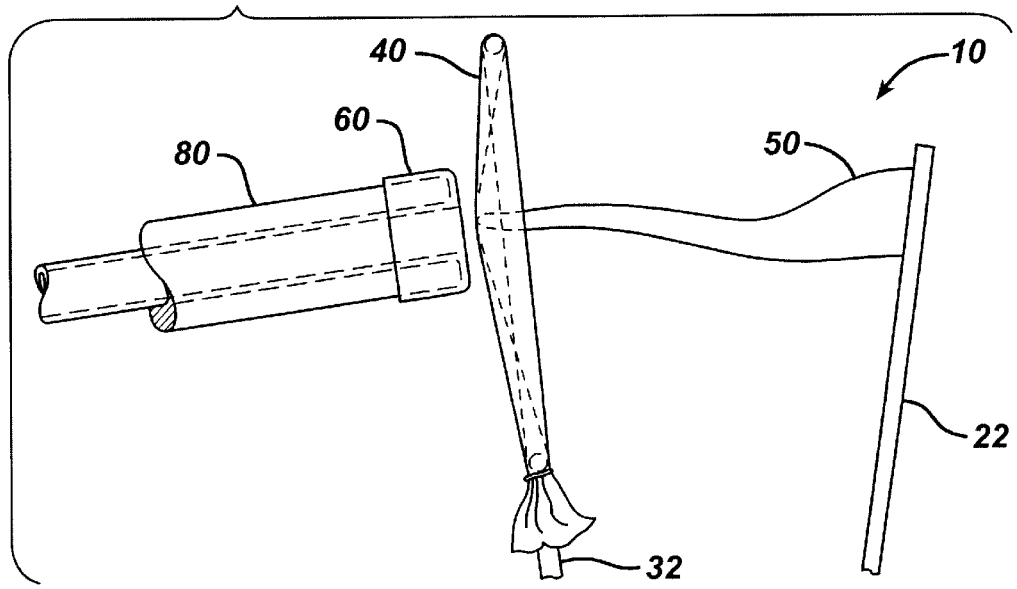

CURVED MANDREL FOR ASSISTING VESSEL EVERSION

FIELD OF THE INVENTION

The field of art to which this invention relates is medical devices, more specifically, medical devices and surgical procedures for performing anastomosis of hollow organs such as blood vessels.

BACKGROUND OF THE INVENTION

Anastomosis surgical procedures are common in the field of cardiac surgery. These procedures are conventionally used for repairing a damaged or diseased blood vessel. In a typical anastomosis procedure, a surgeon joins a first blood vessel to a second blood vessel and creates a passageway between the two blood vessels to provide for the communication of blood flow. For this kind of anastomosis, the surgeon typically uses specialized grasping tools to manipulate a tiny, curved needle attached to an extremely fine surgical filament (under 0.001 inch diameter) to suture the vessels together. The vessels may be joined end-to-end, end-to-side, or side-to-side. To facilitate healing of the joined vessels, the prevailing standard of care requires that the surgeon suture the inside surfaces of the first and second vessels together, intima to intima. The surgeon must take great care not to damage the intima of each vessel so that endothelial cells may form over the anastomosis without the formation of thrombus or other complications, thus improving the likelihood of a long term patency of the vessels. For life-saving procedures such as coronary artery bypass graft surgery (CABG), this is especially important. When performing a distal anastomosis in a conventional CABG procedure, the surgeon typically sutures an end-to-side anastomosis of a distal end of a graft vessel (such as a segment of saphenous vein harvested from the patient) to a side of a target vessel (the stenosed coronary artery). For a proximal anastomosis in a conventional CABG procedure, the surgeon sutures a proximal end of the graft vessel to the side of the aorta.

As this field of art has progressed over the last several years, new anastomotic methods have been developed and introduced in attempts to replace the suturing technique briefly described above. Many of these methods incorporate novel fasteners and fastener appliers. The requirement, however, to maintain intima-to-intima contact of the joined vessels remains just as important with these approaches. In fact it is often necessary, prior to joining the vessels, for the surgeon to evert (i.e., turn inside out) the end of at least one of the vessels over the end of a member such as a tube, ferrule, or bushing, etc., which is a component of the fastener or fastener applier. This exposes the intima of that vessel for presentation to the intima of the other vessel prior to fastening the vessels.

Although it is possible to evert larger vessels (over 5 mm in diameter) using standard forceps and graspers available in the operating room, such methods are slow and may result in excessive damage to the vessel everted. And, often the surgeon requires assistance in performing the eversion procedure. Furthermore, vessels smaller than 5 mm are very difficult, if not impossible, to evert using such methods.

There are several requirements for an effective vessel eversion device. As noted earlier, for proper healing, it is important not to injure the intima of either vessel during the eversion procedure. The eversion device also must be easy for the surgeon to use without assistance and require only a few steps to operate. The eversion device must be useful for a wide range of blood vessel sizes, particularly small vessels, e.g., having a diameter of about 2–3 mm or less. In addition, it is desirable for the eversion device to be useful on one end of a vessel when the opposite end is already attached to the patient (e.g., at the distal anastomosis of a patient undergoing a CABG procedure). The eversion device should also allow for the proper length of everted tissue, depending on the requirements of the anastomosis device or method to be used. Finally, it is desirable that the eversion device is low cost and yet operates reliably.

Accordingly, there is a need in this art for novel devices and methods for engaging and everting the end of a blood vessel (or other tubular body organ) which can be used in a quick and effective manner without causing trauma to the vessel or the intima of the vessel (or tubular body organ).

SUMMARY OF THE INVENTION

It is an object of the present invention to provide novel eversion devices which are easy for the surgeon to use without assistance, and which efficiently and effectively engage blood vessels and evert the ends of blood vessels, including blood vessels having small or fine diameters.

A further object of the present invention is to provide novel eversion devices that engage blood vessels and evert the ends of blood vessels without causing trauma to the blood vessel or the intima of the blood vessels.

It is yet another object of the present invention to provide novel methods of engaging and everting blood vessels quickly and efficiently, while preventing or minimizing damage to the blood vessels and the intimas of the blood vessels.

It is still yet a further object of the present invention to provide a novel vessel eversion device and procedure for everting one end of a vessel having the other end already attached to another vessel.

Accordingly, an eversion instrument for everting an end of a vessel is disclosed.

The instrument has a handle member. There is a curved mandrel member having a proximal end, a distal end, an outer surface and a longitudinal axis. The proximal end of the mandrel member is mounted to the handle member, while the distal end and at least a distal section of the curved mandrel member are insertable to a predetermined depth into the lumen of a vessel contained in the bore of a workpiece having a bore and an inner surface surrounding the bore. The outer surface of the curved mandrel member engages a vessel against the bore surface of the workpiece at three spaced-apart contact regions when the curved mandrel member is inserted into the bore of the workpiece to the predetermined depth Yet another aspect of the claimed invention is a method of everting a vessel. A tubular workpiece is provided. The tubular workpiece has a tubular member having a proximal end, a distal end, an inner bore, an inner surface surrounding the inner bore, and an outer surface. A body vessel, such as a blood vessel, having at least a first end is provided. At least a section of the vessel is placed into the bore of the tubular member. An eversion instrument is provided. The instrument has a handle member. The instrument also has a curved mandrel member having a proximal end, a distal end, an outer surface and a longitudinal axis. The proximal end of the mandrel member is mounted to the handle member. The distal end of the curved mandrel member is insertable to a predetermined depth into the lumen of the vessel contained in the bore of the tubular member, wherein the outer surface of the curved mandrel member engages the vessel against the inner surface of the tubular member at three spaced-apart contact regions when said curved mandrel member is inserted into the vessel lumen and bore to the predetermined depth. At least a distal section of the mandrel member is inserted into the lumen of the vessel contained in the bore of the tubular member and the vessel is engaged against the inner surface of the tubular member by the outer surface of the mandrel member at three spaced-apart contact regions. The end of the vessel is invaginated over the distal end of the tubular member and onto the outer surface of the distal end of the tubular member. Then, the curved mandrel member of said eversion instrument is removed from the lumen of the vessel and the bore of the tubular member, thereby providing an everted end of the vessel.

These and other aspects and advantages of the present invention will become more apparent from the following description and accompanying drawings.

BRIEF DESCRIPTION OF THE DRAWINGS

FIG. 1 is an isometric view of an eversion instrument 10 of the present invention having a membrane 40 shown in a flat configuration;

FIG. 2 is a side view of the eversion instrument 10 of FIG. 1 with membrane 40 in a substantially flat the flat configuration;

FIG. 6 is a partial side view illustrating the distal end of eversion instrument 10 with membrane 40 in an invaginated configuration over tubular workpiece 80;

FIG. 7 is a sectional view of a portion of eversion instrument 10 with membrane 40 in the invaginated configuration over tubular workpiece 80; and FIG. 8 is a side view illustrating the distal end of eversion instrument 10 withdrawn from tubular workpiece 80, with membrane 40 returned to the substantially flat position and vessel 60 everted over the end of tubular workpiece 80.

DETAILED DESCRIPTION OF THE INVENTION

Figure 3:
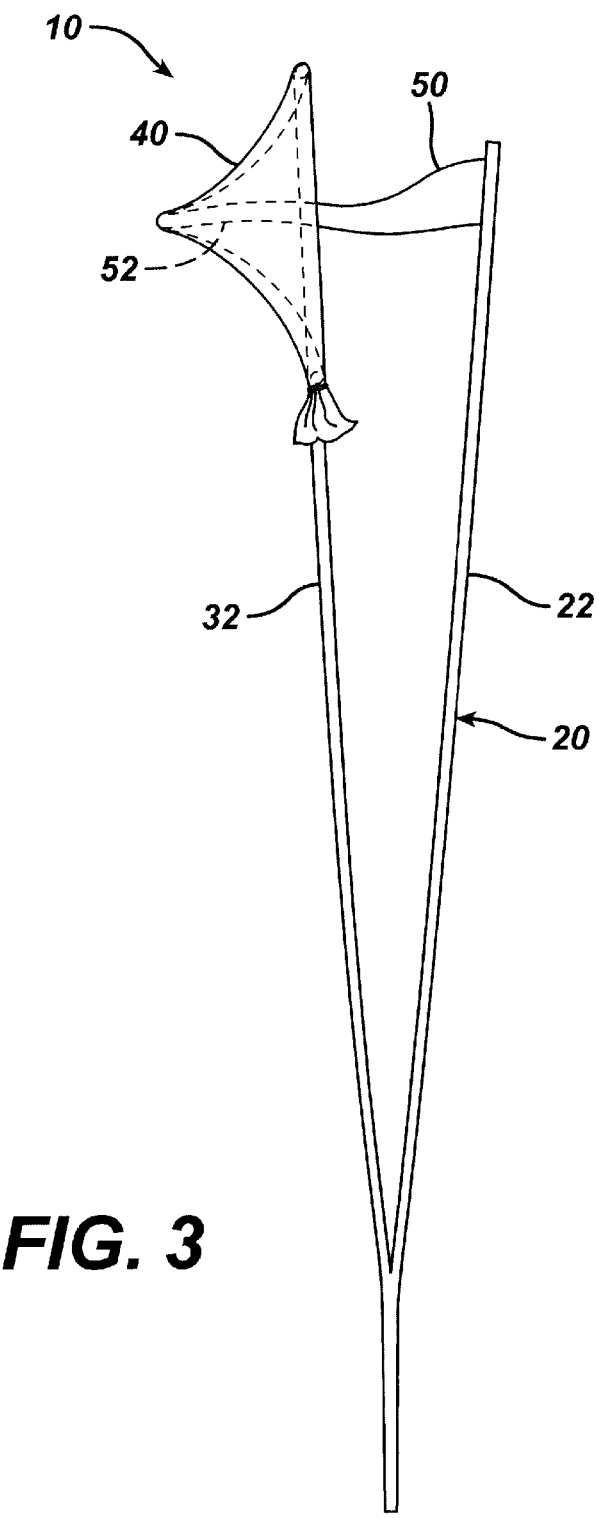
FIG. 3 is a side view of the eversion instrument 10 of FIG. 1 with membrane 40 in a stretched configuration.

The eversion instrument 10 of the present invention is illustrated in FIGS. 1–3. Referring to FIG. 1, the eversion instrument 10 is seen to have a handle frame 20, which resembles a surgical forceps handle. Handle frame 20 is seen to have a first arm 22 and a second arm 32. An angulated proximal end 26 of first arm 22 is attached, preferably by welding although other conventional attachment techniques may be used, to an angulated proximal end 36 of second arm 32. A distal end 24 of first arm 22 is normally spaced apart from a distal end 34 of second arm 32 due to the inherent springiness of first arm 22 and second arm 32. An operator holds handle 20 and squeezes together first arm 22 and second arm 32 to move distal end 24 of first arm 22 and distal end 34 of second arm 32 closer together. When first arm 22 and second arm 32 are allowed to spring to their natural outward resting positions, eversion instrument 10 is in an open configuration. Although not preferred, distal ends 26 and 36 may be mounted together with a conventional hinge, which may be spring loaded or biased. When the operator squeezes together first arm 22 and second arm 32 thereby displacing the arms until they are nearly adjacent, eversion instrument 10 is in a closed configuration. Eversion instrument 10 is further seen to have a ring member 38 attached to distal end 34 of second arm 32. Ring member 38 may be circular with a diameter, or may have other geometric shapes such as rectangular, square, polygonal, oval, triangular, combinations thereof and the like. The diameter is sufficiently effective for mounting a membrane, for example, preferably approximately in the range of 30–50 mm, although it is not restricted to this size or shape. A membrane 40 (also referred to as an elastic diaphragm) is seen to be mounted over ring 38 and optionally is retained by a membrane tie 42. Membrane 40 has an inside membrane surface 46 and an outside membrane surface 44. Membrane 40 is made from a conventional elastic material such as latex rubber or silicone and equivalents thereof and the like having sufficient elasticity to effectively be deformed and then return to an original flat configuration. Membrane 40 may be made from any one of numerous existing products including a finger cot, a portion of a balloon, or a finger portion of a surgical glove, the latter of which is readily available in a hospital operating room where the device is used. Membrane 40 may easily be replaced, therefore, should it become torn or punctured. Eversion instrument 10 is further seen to have a curved mandrel member 50.

Eversion instrument 10 is shown in an open configuration in FIG. 2. The curved mandrel member 50 is seen to extend laterally from distal end 24. Mandrel 50 is seen to have a slender distal tip 52 that tapers gradually to a wider proximal end 54 that is attached to distal end 24 of first arm 22. Mandrel member 50 is also seen to have an outer surface 56. Curved mandrel 50 has a longitudinal axis 51 that is preferably substantially perpendicular to membrane 40, such that distal tip 52 pushes lightly on membrane 40 near the center 41. Distal tip 52 may also be spaced apart from membrane 40 when eversion instrument 10 is in the open configuration. Curved mandrel 50 may be made from conventional biocompatible materials including metals, ceramics, polymeric materials, or other rigid material, but is preferably made from a moderately flexible polymeric material such as, for example, high density polyethylene (HDPE).

Referring now to FIG. 3, eversion instrument 10 is seen in the closed configuration. The operator's hand (not shown for clarity) squeezes first arm 22 and second arm 32 of handle 20 close together. Curved mandrel 50 engages and elastically deforms or stretches membrane 40, which conforms tightly to distal tip 52.

Figure 4:
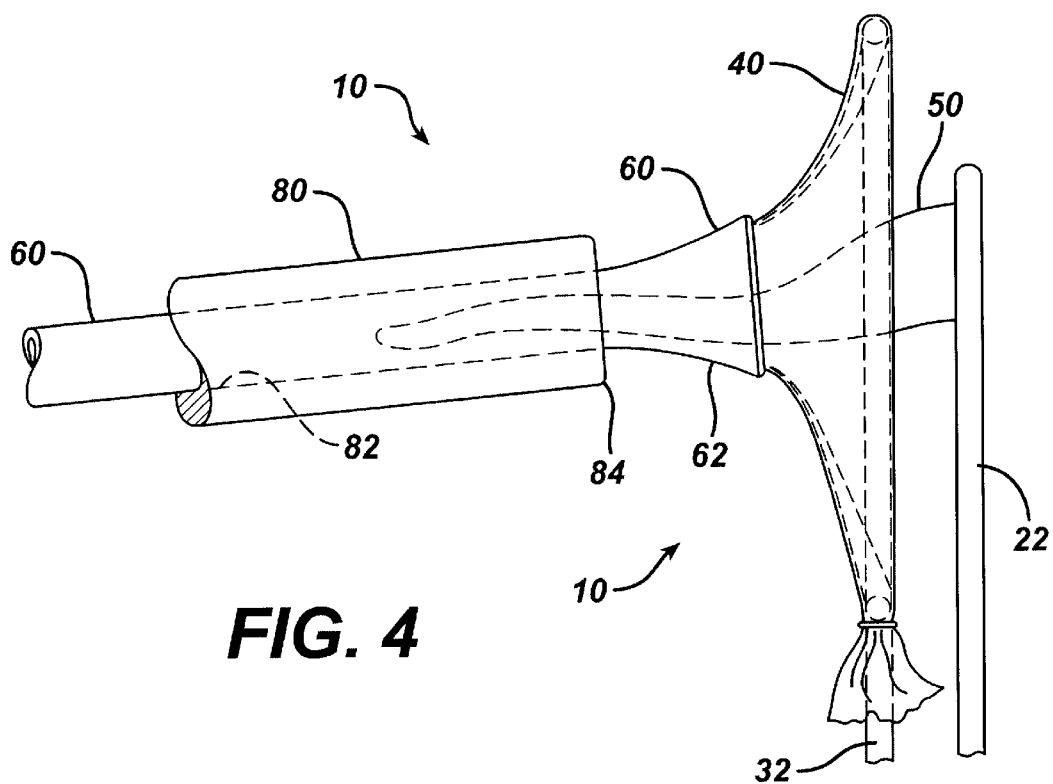
FIG. 4 is an enlarged, partial view of a the distal end of eversion instrument 10 illustrating membrane 40 in the stretched configuration and inserted into a vessel 60, which is held in a tubular workpiece 80.

The operation of eversion instrument 10 is illustrated in FIGS. 4–8. As seen in FIG. 4, eversion instrument 10 is positioned to have mandrel 50 engaging membrane 40 with a portion of stretched membrane 40 inserted into a lumen 65 of a vessel 60 contained in a tubular member 80. Vessel 60 may be a blood vessel, although other hollow organs may be everted using eversion instrument 10. For example, blood vessels having a diameter of about 2 to about 8 mm may be everted using eversion instrument 10 of the present invention. A tubular workpiece 80 holds vessel 60 and is representative of numerous kinds of bushings, ferrules, tubes, and specialized devices having an approximately cylindrical shape with an axial bore through it. (Throughout the description of the use of eversion instrument 10, it is assumed that the operator, an assistant, or a mechanical holding device is holding tubular workpiece 80 in a stationary position; the term operator as used herein is meant to mean surgeon or other health care professional.) Before eversion instrument 10 is inserted into the lumen 65 of vessel 60, vessel 60 must be positioned within an axial bore 82 of tubular workpiece 80 so that an extended end portion 62 of vessel 60 extends beyond an end 84 of tubular workpiece 80. The length of extended portion 62 of vessel 60 depends partially on the desired length of eversion and is sufficiently long to provide effective eversion, preferably in the range of about 5–15 mm.

Figure 5:
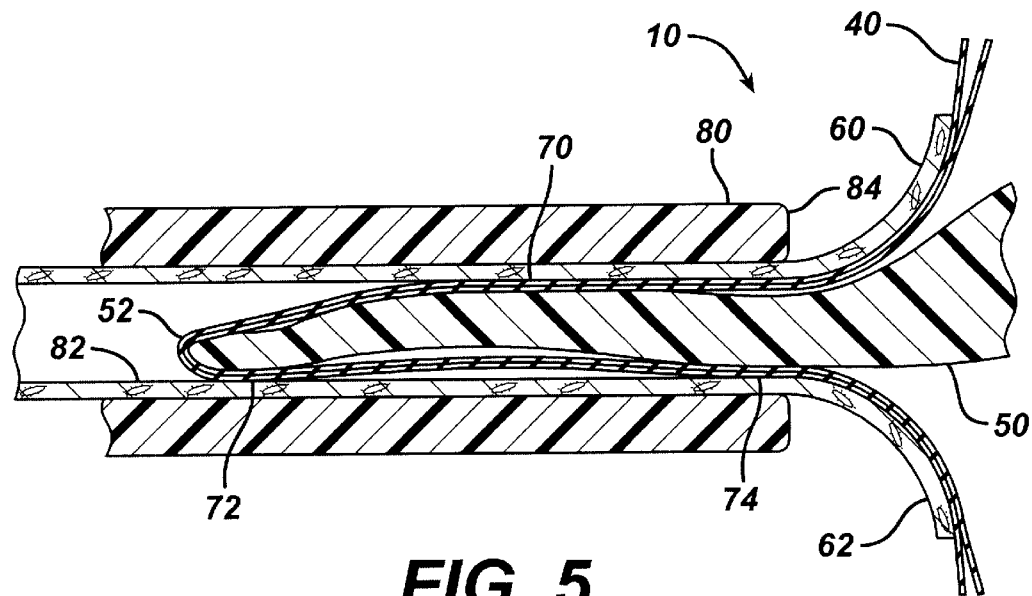
FIG. 5 is a partial cross-sectional side view of a section of eversion instrument 10 with membrane 40 in a stretched configuration and inserted into vessel 60, which is held in tubular workpiece 80.

FIG. 5 is a sectional view showing mandrel 50 and a section of membrane 40 inserted into the lumen 65 of vessel 60. Vessel 60 is seen to be held by tubular workpiece 80. Distal tip 52 of curved mandrel 50 is slender enough to fit easily into lumen 65 of vessel 60, and positions a section of membrane 40 inside vessel 60. The length of the section of curved mandrel 50 positionable inside tubular workpiece 80 is predetermined due to the shape and flexibility of curved mandrel 50 and may vary and is sufficiently long to effectively engage the membrane 40 and lumen 65 of vessel 60, and for example is preferably in the range of about 10–20 mm. The outer surface 56 of curved mandrel 50 presses membrane 40 and vessel 60 against interior surface 85 in axial bore 82 at a first contact location 70, and at two other opposing locations: a second contact location 72 and a third contact location 74. For the embodiment in which curved mandrel 50 is made from a flexible material, as the operator inserts curved mandrel 50 into lumen 65 of vessel 60, distal tip 52 flexes. In this way the first, second, and third contact locations, 70, 72, and 74, are established but the pressure on vessel 60 at these locations is substantially limited by the degree of flexibility of curved mandrel 50. Vessel 60, therefore, is securely held inside axial bore 82 and prevented from receding deeper into tubular workpiece 80, thus maintaining the length of extended portion 62 as it is everted over end 84 of tubular workpiece 80 onto the outer surface 88 of tubular workpiecde 80. As a result, the intended length of everted tissue for the purpose of anastomosis may be obtained without numerous trials.

FIG. 6 is a view of a portion of eversion instrument 10 as it is used to complete the eversion of end 64 of vessel 60 over the distal end 84 of tubular workpiece 80. Membrane 40 invaginates as the operator moves second arm 32 beneath tubular workpiece 80 and ring member 38 about tubular member 80 while allowing first arm 22 to stop at the position shown when the wider proximal end 34 of curved mandrel 50 cannot be inserted any further into tubular workpiece 80. As ring 38 is passed over tubular workpiece 80, membrane 40 everts or flips end section 62 of vessel 60 inside out.

FIG. 7 is a cross-sectional view of vessel end section 62 everted over tubular workpiece 80 while membrane 40 is still invaginated as shown in FIG. 6. The operator may push second arm 32 (FIG. 6) and stretch membrane 40 to the limit of the membrane material elasticity without damaging vessel 60.

FIG. 8 illustrates the distal end portion of eversion instrument 10 as mandrel 50 and membrane 40 are withdrawn from and about vessel 60 and tubular workpiece 80. Membrane 40 returns to a flat configuration as first arm 22 and second arm 32 are released and permitted to spring apart or displace apart from each other, so that curved mandrel 50 comes out of vessel 60. The operator may repeat the operational sequence, several times if necessary, to achieve the desired quality of eversion of vessel 60.

Handle member 20 shown in FIGS. 1 and 2 is not restricted to a forceps style handle. Other styles of handles for holding membrane 40 while moving mandrel 50 and everting vessel 60 over a tubular workpiece 80 as already described will be recognized by those skilled in the art. For example, membrane 40 may be attached over the end of a cylinder, with mandrel 40 attached to a spring loaded piston within an axial bore of the cylinder, so that the piston may be advanced and retracted to configure membrane 40 from the open position to the stretched position, and back to the open position.

In an alternate embodiment, eversion instrument 10 may also be used without membrane 40 to hold vessel 60 securely in tubular workpiece 80 while another conventional, surgical instrument such as a forceps, grasper, or probe is used to evert vessel 60 over tubular workpiece 80. In still another alternate embodiment, eversion instrument 10 comprises curved mandrel 50 attached to arm 22, although the shapes and styles of curved mandrel 50 and arm 22 are not restricted to the embodiment shown in FIG. 1, and may include curved mandrel 50 and arm 22 being constructed as a single injection moldable plastic element.

The advantages of the eversion instrument and method of use of the present invention in everting blood vessels are numerous. The advantages include the following. The present invention incorporates resilient materials that are relatively atraumatic to the vessel walls. The device requires only a few easy steps to operate, which may be rapidly repeated as required until the eversion is achieved. The eversion device is useful for a wide range of vessel sizes and may be used on an end of a vessel even if the opposite end is attached to the body or another device. The eversion device effectively holds the vessel inside the axial bore of the tubular workpiece during the eversion. Also, the present invention is very simple and inexpensive to manufacture, and may readily be adapted into a single-patient-use, disposable device.

Although this invention has been shown and described with respect to detailed embodiments thereof, it will be understood by those skilled in the art that various changes in form and detail thereof my be made without departing from the spirit and scope of the claimed invention.

What is claimed is:

1. An instrument for everting an end of a vessel, comprising:
    a workpiece having a bore and an inner surface, the workpiece dimensioned to permit the vessel to be disposed at least partially within the bore;
    a curved mandrel member having a proximal end, a distal end, an outer surface and a longitudinal axis, said distal end of said curved mandrel member insertable to a predetermined depth into a lumen of the vessel, said outer surface of said curved mandrel member configured to engage the vessel against the inner surface of the workpiece at three spaced-apart locations when said curved mandrel member is inserted into the bore to said predetermined depth.

2. The instrument of claim 1, wherein said curved mandrel is flexible.

3. The instrument of claim 1, wherein said curved mandrel tapers from a first diameter on said proximal end to a smaller, second diameter on said distal end.

4. The instrument of claim 1, further comprising:
    a handle;
    a frame having an axial bore, and an elastic diaphragm mounted on said frame and covering said axial bore, wherein said frame is mounted to said handle such that said mandrel member is moveable with respect to said frame to distend said diaphragm.

5. The instrument of claim 4, wherein said diaphragm comprises a section of a rubber surgical glove and is removably mounted on said frame.

6. The instrument of claim 4, comprising wherein said handle comprises a first arm and a second arm, and said diaphragm is mounted on said frame attached to said first arm, and said proximal end of said curved mandrel is mounted on said second arm.

7. A method for everting a vessel, comprising the steps of:
   providing a workpiece comprising a tubular member having a proximal end, a distal end, an inner bore, and an inner surface surrounding the inner bore, and an outer surface;
   providing a vessel having at least a first end and a lumen;
   placing at least a section of the vessel in the bore of the tubular member;
   providing an eversion instrument, comprising:
      a mandrel member having an outer surface:
      inserting at least a distal section of the mandrel member into the lumen of the vessel;
      engaging the vessel against the inner surface of the tubular member with the outer surface of the mandrel member at three spaced-apart locations;
      everting the end of said vessel over the distal end of said tubular member and onto the outer surface of distal end of the tubular member.

* * * * *